US010226300B2

(12) United States Patent
Ng et al.

(10) Patent No.: US 10,226,300 B2
(45) Date of Patent: Mar. 12, 2019

(54) SYSTEM AND METHOD FOR ALIGNING AN ELONGATED TOOL TO AN OCCLUDED TARGET

(71) Applicant: NDR Medical Technology Pte. Ltd., Singapore (SG)

(72) Inventors: Ka Wei Ng, Singapore (SG); Jin Quan Goh, Singapore (SG); Ting Liu, Singapore (SG); Jun Wen Foong, Singapore (SG)

(73) Assignee: NDR Medical Technology Pte. Ltd., Primz Bizhub (SG)

( * ) Notice: Subject to any disclaimer, the term of this patent is extended or adjusted under 35 U.S.C. 154(b) by 412 days.

(21) Appl. No.: 15/211,724

(22) Filed: Jul. 15, 2016

(65) Prior Publication Data
US 2017/0014193 A1    Jan. 19, 2017

(51) Int. Cl.
*A61B 6/00* (2006.01)
*A61B 34/20* (2016.01)
*A61B 34/30* (2016.01)
*A61B 17/00* (2006.01)
*A61B 17/34* (2006.01)
*A61B 90/00* (2016.01)

(52) U.S. Cl.
CPC .............. *A61B 34/20* (2016.02); *A61B 6/487* (2013.01); *A61B 34/30* (2016.02); *A61B 2017/0092* (2013.01); *A61B 2017/3407* (2013.01); *A61B 2034/2055* (2016.02); *A61B 2034/2065* (2016.02); *A61B 2034/2074* (2016.02); *A61B 2034/304* (2016.02); *A61B 2090/376* (2016.02); *A61B 2090/3966* (2016.02)

(58) Field of Classification Search
CPC .... A61B 2014/0092; A61B 2017/3407; A61B 2034/2055; A61B 2034/2065; A61B 2034/2074; A61B 2034/304; A61B 2090/376; A61B 2090/3966; A61B 34/20; A61B 34/30; A61B 2034/2059; A61B 6/487
See application file for complete search history.

(56) References Cited

U.S. PATENT DOCUMENTS

2006/0229641 A1* 10/2006 Gupta ................ A61B 17/3403
606/130

* cited by examiner

*Primary Examiner* — Dani Fox
(74) *Attorney, Agent, or Firm* — Wood, Philips, Katz, Clark & Mortimer (57) ABSTRACT

A system and a method for aligning an elongated tool to an occluded target are disclosed. The system comprises an adjustment mechanism configured to adjust an angular orientation of the elongated tool relative to a pivot point spaced from the target; an imaging device configured to capture one or more X-ray images of the elongated tool and the target; and a processor communicatively coupled with the adjustment mechanism and imaging device, wherein the processor is configured to: extract Euclidean vector data of the elongated tool based on image data of an X-ray image received from the imaging device; and control the adjustment mechanism to iteratively adjust the angular orientation of the elongated tool based on the Euclidean vector data to align a longitudinal axis of the elongated tool with the target and the pivot point.

17 Claims, 9 Drawing Sheets

SYSTEM AND METHOD FOR ALIGNING AN ELONGATED TOOL TO AN OCCLUDED TARGET

FIELD OF INVENTION

The present invention relates broadly to a system and method for aligning an elongated tool to an occluded target.

BACKGROUND

Percutaneous access to the kidney (PAK) or renal access is a minimally invasive procedure for establishing a keyhole access in percutaneous nephrolithotomy (PCNL) to remove a kidney stone. In this procedure, a trocar is passed through a patient's skin through the body layers into the kidney to reach a stone target. Surgical instruments such as guidewire, ultrasonic probes and vacuum are then passed through the hole in the trocar to carry out the stone removal process.

Conventionally, a PAK procedure is carried out by a surgeon holding a trocar in his hand with one end of the trocar resting on a patient's skin. The other end of the trocar is tilted numerous times to establish an accurate alignment between the trocar and the stone target. The alignment of the trocar is determined with the help of a C-arm fluoroscope. Once the accurate alignment is confirmed, the surgeon has to maintain the alignment of the trocar by steadying his hand. The trocar is subsequently pushed into the patient's body to reach the stone target.

The duration of the trocar insertion procedure typically ranges from 10 minutes to 1.5 hours and throughout the procedure, the C-arm fluoroscope has to be in operation. Consequently, both the patient and surgical crew are subjected to long exposure of X-ray and this could be a potential health hazard in the long run. In addition, due to the elaborate procedure, there may be instances when the trocar has to be withdrawn and the entire procedure needs to be repeated. This may aggravate the condition of the patient as multiple punctures of the kidney may increase the risks to the patient such as significant bleeding, haematoma formation and infection. The procedure may have to be called off and rescheduled, thus causing much distress to the patient and loss of precious time of the healthcare professionals.

To address the problems above, robotic arms are used to perform the trocar insertion procedure. For example, current approaches utilise robotic arm surgical systems which mimic the standard manual percutaneous renal access. In other words, the systems are manually controlled by the surgeon, e.g. using a manipulator such as a joystick, to align the trocar with the kidney stone. Also, these conventional systems are bulky and slow in processing. It is also expensive to manufacture the systems and implement the trocar insertion procedure using the systems.

A need therefore exists to provide a system for aligning a surgical tool that seeks to address at least some of the above problems.

SUMMARY

According to a first aspect of the present invention, there is provided system for aligning an elongated tool to an occluded target, the system comprising:

an adjustment mechanism configured to adjust an angular orientation of the elongated tool relative to a pivot point spaced from the target;

an imaging device configured to capture one or more X-ray images of the elongated tool and the target; and a processor communicatively coupled with the adjustment mechanism and imaging device, wherein the processor is configured to:

extract Euclidean vector data of the elongated tool based on image data of an X-ray image received from the imaging device; and control the adjustment mechanism to iteratively adjust the angular orientation of the elongated tool based on the Euclidean vector data to align a longitudinal axis of the elongated tool with the target and the pivot point.

The Euclidean vector data may comprise an image length of the elongated tool on an X-ray image and wherein the processor may be configured to determine said image length.

The processor may be configured to:

determine the image length of the elongated tool based on the X-ray image of the elongated tool at a first angular orientation; and automatically control the adjustment mechanism to adjust the elongated tool to a second angular orientation based on the image length if the image length is not approximately equal to a minimum, to iteratively align the longitudinal axis of the elongated tool with the target and the pivot point.

The adjustment mechanism may comprise a base and a platform, wherein the platform may be configured to be parallel to the base.

The adjustment mechanism may further comprise a plurality of arms linking the base with the platform, the plurality of arms may be configured to move the platform along a plane parallel to the base to adjust the angular orientation of the elongated tool relative to the pivot point.

The platform may comprise a ball joint compliance for supporting the elongated tool, the ball joint compliance may comprise a hole configured to allow sliding movement of the elongated tool there through.

The base of the adjustment mechanism may be made of a radiopaque material and wherein remaining components of the adjustment mechanism may be made of one or more radiolucent materials.

The imaging device may be a C-arm fluoroscope configured to capture real-time X-ray images.

The adjustment mechanism may further comprise at least one actuator communicatively coupled with the processor, the actuator may be configured to operate the arms.

According to a second aspect of the present invention, there is provided a method of aligning an elongated tool to an occluded target, the method comprising the steps of capturing one or more X-ray images of the elongated tool and the target;

extracting Euclidean vector data of the elongated tool based on image data of an X-ray image; and iteratively adjusting an angular orientation of the elongated tool relative to a pivot point based on the Euclidean vector data to align a longitudinal axis of the elongated tool with the target and the pivot point.

The Euclidean vector data may comprise an image length of the elongated tool on an X-ray image.

Adjusting an angular orientation may comprise the steps of:

determining the image length of the elongated tool based on the X-ray image at a first angular orientation; and automatically controlling the adjustment mechanism to adjust the elongated tool to a second angular orientation based on the image length if the image length is not approximately equal to a minimum, to iteratively align the longitudinal axis of the elongated tool with the target and the pivot point.

The method may further comprise a step of calibrating a geometrical relationship between an imaging device capturing the one or more X-ray images and an adjustment mechanism adjusting the angular orientation of the elongated tool.

Calibrating may comprise determining the number of iterations to reach the minimum from an initial image length.

The adjustment mechanism may comprise a base and a platform parallel to the base, and the step of calibrating may comprise fixing a height of the platform from the base.

According to a third aspect of the present invention, there is provided a method of striking an occluded target using an elongated tool, the method comprising the step of:

iteratively advancing the elongated tool toward the target, wherein iteratively advancing the tool comprises aligning the tool to the target at each iteration using the method as claimed in the second aspect.

The method may further comprise a step of determining a distance between a tip of the tool and target after a predetermined number of iterations.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
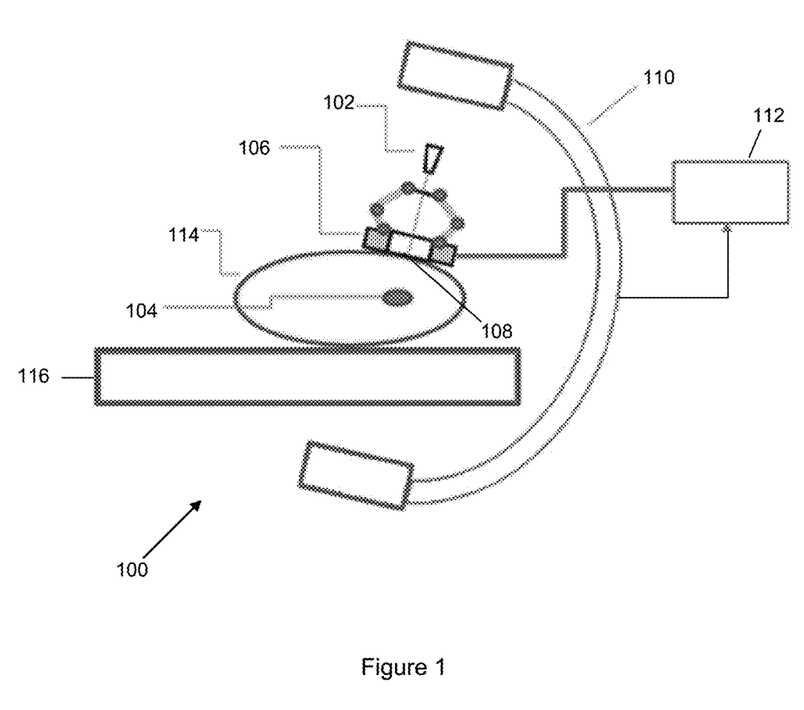
FIG. 1 shows a schematic diagram illustrating a system for aligning an elongated tool to an occluded target according to an example embodiment.

FIG. 1 shows a schematic diagram illustrating a system 100 for aligning an elongated tool, for example a surgical tool 102 such as a hollow needle, to an occluded target 104 according to an example embodiment. In the description that follows, the system 100 is described with reference to a surgical application and the occluded target is a kidney stone 104. However, it will be appreciated that the system 100 can be used in numerous other applications.

The system 100 comprises an adjustment mechanism 106. The adjustment mechanism 106 is configured to adjust an angular orientation of the surgical tool 102 relative to a pivot point 108. The system 100 further comprises an imaging device, in the form of a C-arm fluoroscope 110, configured to capture one or more X-ray images of the surgical tool 102 and the occluded target, for example, a kidney stone 104. The system 100 further comprises a processor 112 communicatively coupled with the adjustment mechanism 106 and the C-arm fluoroscope 110. The processor 112 is configured to extract Euclidean vector data of the surgical tool 102 based on an X-ray image data received from the C-arm fluoroscope 110 and control the adjustment mechanism 106 to iteratively adjust the angular orientation of the surgical tool 102 based on the Euclidean vector data to align a longitudinal axis of the surgical tool 102 with the kidney stone 104 and the pivot point 108.

In this embodiment, the adjustment mechanism 106 may be mounted on a patient's body 114 lying on a surgical table 116, e.g. using adhesive tape or gel. In other words, the adjustment mechanism 104 is not connected to a fixed structure, but rather, can be positioned at a desired place relative to the patient for the required type of surgery. The adjustment mechanism 106 mounted on the patient's body 114 may move in tandem with the breathing movement of the patient's abdomen. This may minimize skin and organ rupture during the operation when the surgical tool 116 is in the patient's body 114. In other embodiments, the adjustment mechanism 106 may be mounted to a rigid structure above the patient's body 114 and surgical table 116 to fix the position of the adjustment mechanism 106. The adjustment mechanism 106 includes at least one actuator (not shown) that is configured to operate the adjustment mechanism 106 when the actuator receives signals from the processor 112 via a wireless connection. In yet another embodiment, the signals from the processor 112 may also be transmitted to the actuator via a wired connection.

The C-arm fluoroscope 110 may capture real-time X-ray images of the surgical tool 102 and the kidney stone 104. The position on the skin of the patient's body 114 adjacent to the kidney stone 104 is typically marked with an "X" mark as the insertion point of the surgical tool 102. In an embodiment, the "X" mark is the pivot point 108 where a tip of the surgical tool 102 is placed when the angular orientation of the surgical tool 102 is being adjusted by the adjustment mechanism 106. Before the adjustment of the surgical tool 102, the position of the C-arm fluoroscope is adjusted to be aligned with the pivot point 108 and the kidney stone 104, such that the pivot point 108 is superimposed on the kidney stone 104 on the X-ray image.

The processor 112 is communicatively coupled to the C-arm fluoroscope 110 to receive the X-ray image data. From the X-ray image data, the processor 112 can extract information such as Euclidean vector data of the surgical tool 102. The Euclidean vector data of the surgical tool 102 in the example embodiments is the length of the surgical tool 102 on the X-ray image and also the orientation of the surgical tool 102, which may be determined by the processor 112. For example, the length of the surgical tool 102 on the X-ray images is the top view of the surgical tool 102. By iteratively adjusting the angular orientation of the surgical tool 102 based on the Euclidean vector data using the adjustment mechanism 106, the distance on the X-ray image is reduced to a predetermined minimum length, typically zero (singularity) where the surgical tool 102 appears as a round dot on the X-ray image, to align the longitudinal axis of the surgical tool 102 with the kidney stone 104. The surgical tool 102 is then inserted into the patient's body 114.

Figure 2A:
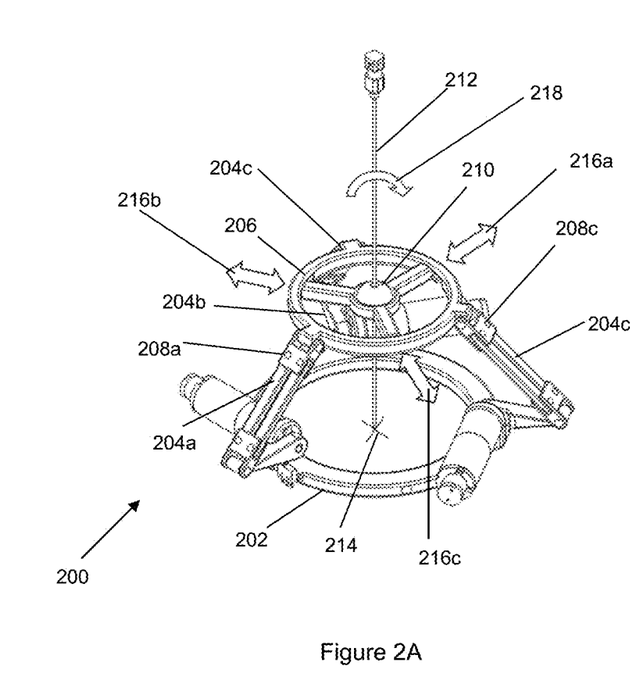
FIG. 2A shows a perspective view of an adjustment mechanism for use in the system of FIG. 1 according to an example embodiment.
Figure 2B:
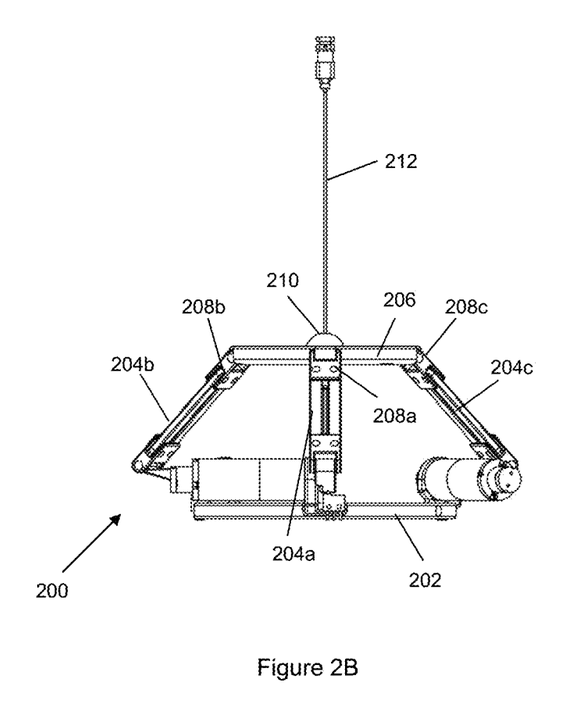
FIG. 2B shows a front view of the adjustment mechanism of FIG. 2A.

FIGS. 2A and 2B show a perspective view and front view respectively of an adjustment mechanism 200 suitable for use in the system 100 of FIG. 1 according to an example embodiment. The adjustment mechanism 200 comprises a base 202, in the form of an annular ring, and a plurality of arms, represented as first arm 204*a*, second arm 204*b* and third arm 204*c*. The arms 204*a*, 204*b*, 204*c* are connected to the base 202 at a substantially uniform angular distance from each other. The adjustment mechanism 200 further comprises a raised platform 206. The raised platform 206 is connected to end effectors 208*a*, 208*b*, 208*c* of the arms 204*a*, 204*b*, 204*c* respectively. The platform 206 comprises a universal or ball joint compliance 210, at the centre of the platform 206. The universal or ball joint compliance 210 comprises a hole which holds a surgical tool 212 and allows sliding movement of the surgical tool 212. The universal or ball joint compliance 210 further comprises a drive mechanism, in the form of a plunger (not shown), for holding and inserting the surgical tool 212 into a patient's body 114 (FIG. 1).

During operation, the base 202 is adhered to the patient's body 114. The arms 204*a*, 204*b*, 204*c* are actuated by at least one actuator (not shown) to coordinate with each other to adjust the position of the platform 206 and thus the orientation and trajectory of the surgical tool 212 relative to the pivot point 214. The platform 206 typically moves at the same plane at a predetermined constant height relative to the base 202 during each operation, and the movement of the platform 206 is shown in FIG. 2A by arrows 216*a*, 216*b*, 216*c* of the platform 206 relative to the base 202. The height is normally determined at the calibration stage prior to the operation based on factors such as needle gauge, patient's physiology etc. When the position of the platform 206 is adjusted by the arms 204*a*, 204*b*, 204*c*, the surgical tool 212 is held loosely by the plunger and the universal or ball joint compliance 210, allowing the surgical tool 212 to pivot or swivel freely about the pivot point 214. This configuration allows tilting of the surgical tool 212 when the platform 206 is moved at the same plane, and the tilting of the surgical tool 212 is shown by arrow 218 in FIG. 2A. After the orientation of the surgical tool 212 is confirmed, the position of the universal or ball joint compliance 210 is locked and the plunger is actuated by the actuator to hold and insert the surgical tool 212 into the patient's body.

The structure of the adjustment mechanism 200 is typically made of light and rigid material. In some embodiments, the adjustment mechanism 200 is made of radiolucent or radio transparent material, such that the X-ray image provided by an imaging device 110 (FIG. 1) does not capture an image of the robot 200. In preferred embodiments, different parts of the adjustment mechanism can be made of materials with different radiolucency. As an example, the base 202 of the adjustment mechanism 200 can be made of radiopaque material, e.g. stainless steel, while other parts of the robot are made of radiolucent material. This may assist in determining the geometrical relationship between the plane formed by the base 202 (hence the plane formed by the platform 206) and an imaging plane of the imaging device 110 during calibration.

As the adjustment mechanism 200 has a simple structure and is relatively small in size, it may move and respond fast to signals from the processor 112 (FIG. 1). The configuration of the adjustment mechanism 200 also restricts excessive movement. This may reduce the tearing of skin in the operation. In addition, most parts of the adjustment mechanism 200 are also made of biocompatible material, such that the use of the adjustment mechanism 200 in the surgery does not cause any undesirable effects to the patient. For example, the materials that may be suitable are titanium and polyether ether ketone (PEEK). However, it will be appreciated that the structure of the adjustment mechanism 200 may be made by other materials.

In an embodiment, the surgical tool 212 may comprise a tactile sensor (not shown) communicatively coupled to the processor 112 to detect pressure change on the surgical tool 212. This may enhance the accuracy of the processor 112 in detecting the depth of the surgical tool 212 in the patient's body and detecting the kidney stone 104 (FIG. 1).

Figure 3:
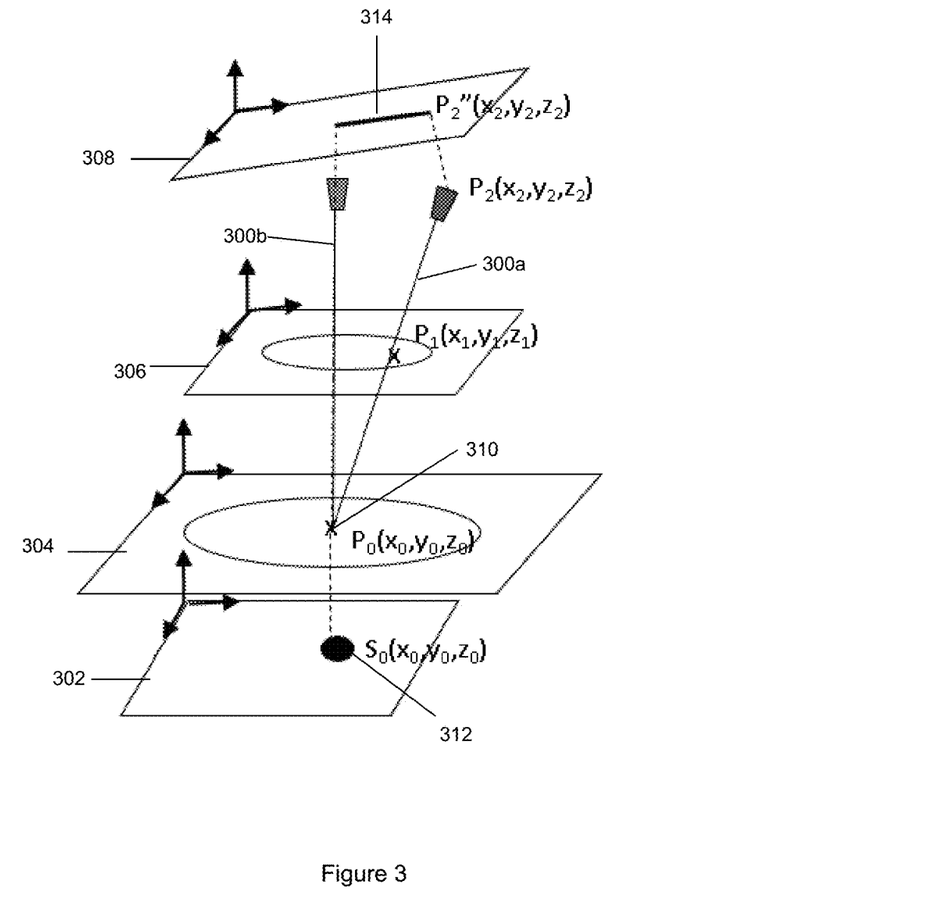
FIG. 3 shows a schematic diagram of a longitudinal axis of the surgical tool being adjusted to align with a target.

FIG. 3 shows a schematic diagram of a longitudinal axis of the surgical tool 102 (FIG. 1) being adjusted to align with a target 312 according to an example embodiment. As shown in FIG. 3, there are four planes involved in the adjustment of the surgical tool 102 from a first angular orientation 300*a* to a second angular orientation 300*b*, i.e. a target plane 302, a pivot point plane 304, an adjustment mechanism plane 306 and an imaging plane 308.

The adjustment mechanism 106 (FIG. 1) moves at the adjustment mechanism plane 306, adjusting the surgical tool 102, and the imaging device 110 (FIG. 1) moves at the imaging plane 308, reflecting and capturing the movement of the surgical tools 102. Before the adjustment of the surgical tool 102 using the adjustment mechanism 106, the imaging plane 308 is adjusted such that a pivot point 310 superimposes on a kidney stone 312 on the X-ray image provided by the imaging device 110. For example, the imaging plane 308 is parallel to the pivot point plane 304.

Here, the length 314 of the surgical tool is superimposed on the imaging plane 308 when the orientation of the surgical tool 102 is at the first angular orientation 300*a*. When the angular orientation of the surgical tool 102 is adjusted by the adjustment mechanism 106 at the adjustment mechanism plane 306 to the second angular orientation 300*b*, the length 314 is shortened to a minimum or singularity, such that the longitudinal axis of the surgical tool 102 is aligned with the kidney stone 312.

Figure 4:
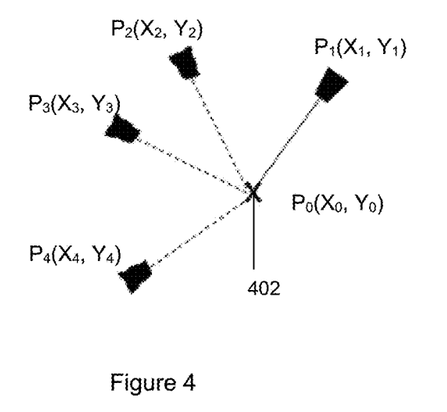
FIG. 4 shows a schematic diagram of multiple X-ray image of the surgical tool during calibration of the adjustment mechanism of FIG. 1.

FIG. 4 shows schematic diagram of multiple X-ray images of the surgical tool 102 (FIG. 1) during calibration of the adjustment mechanism 106 (FIG. 1) according to an example embodiment. The position of a point in a Euclidean space can be considered a Euclidean vector with respect to the origin. The Euclidean distance between two points in a Euclidean space can be determined by the length of the line segment connecting the two points. For example, points $P_1$ to $P_4$ are Euclidean vectors from the origin $P_0$ of the space. In an embodiment, a tip of the surgical tool 102 is placed at a pivot point 402 and an angular orientation of the surgical tool 102 is adjusted by an adjustment mechanism 106 relative to the pivot point 402, which is also the origin $P_0$ of the space.

In the example embodiments, the coordinates of the points along X-axis and Y-axis in the X-ray image data are used to determine the Euclidean distance or image length of the surgical tool 102 on the X-ray image. Thus, point $P_0$ in FIG. 4 has the Cartesian coordinates of $(X_0, Y_0)$ and point $P_1$ has the Cartesian coordinates of $(X_1, Y_1)$ in the Euclidean space and the Euclidean distance can be determined using a Pythagorean formula:

$$d(P_0, P_1) = \sqrt{(X_1-X_0)^2 + (Y_1-Y_0)^2}$$

The Euclidean vector data of the surgical tool 102 at $P_4$ may be extracted by the processor 112 (FIG. 1) based on an X-ray image provided by the imaging device 110 (FIG. 1).

The processor 112 may determine the image length of the surgical tool 102 on the X-ray image. The processor 112 then transmits signal to an actuator to control the adjustment mechanism 106 to iteratively adjust the angular orientation of the surgical tool 102 based on the determined image length of the surgical tool 102. The step of determining the image length of the surgical tool 102 and controlling the adjustment mechanism 106 to adjust the angular orientation of the surgical tool 102, as discussed above, may be repeated automatically until the image length reaches a minimum where the surgical tool 102 superimposes on the pivot point 108 (FIG. 1) on the X-ray image. The minimum length, e.g. zero, indicates that the longitudinal axis of the surgical tool 102 is substantially aligned with the kidney stone 104 (FIG. 1).

The position of the imaging device 110 relative to the adjustment mechanism 106 can be determined and calibrated using various methods. In an embodiment, the calibration of the adjustment mechanism 106 and the imaging device 110 may be performed by extracting the shape of a radiopaque base 202 (FIG. 2) of the adjustment mechanism 106 from the X-ray image provided by the imaging device 110 and determine the position of the imaging device 110 from the shape of the base 202. In another embodiment, the processor 112 may be configured to move the platform 206 (FIG. 2) of adjustment mechanism 106 along the adjustment mechanism plane 306 (FIG. 3) at predetermined steps, allowing a processor 112 to superimpose the imaging plane 308 onto the adjustment mechanism plane 306. Specifically, the calibration may be conducted by mapping the adjustment mechanism plane 306 to the imaging plane 308. This includes mapping the adjustment mechanism plane 306 resolution to the imaging plane 308 resolution and vice versa, to determine the relationship of both the planes. The calibration may compensate the angular errors resulted from the angular differences between the planes.

In an embodiment, the relationship between the changes in the Euclidean vector data of the surgical tool 102 for a certain movement caused by the adjustment mechanism 106 may be determined by the processor 112 using statistical processes, such as regression analysis. The information may be used to determine the calibration of the adjustment mechanism 106, such that the movement of the adjustment mechanism 106 based on the Euclidean vector data of the surgical tool 102 may become more accurate. In other words, the calibration may enhance the accuracy of the processor 112 in controlling the adjustment mechanism 106 based on the Euclidean vector data of the surgical tool 102.

Figure 5:
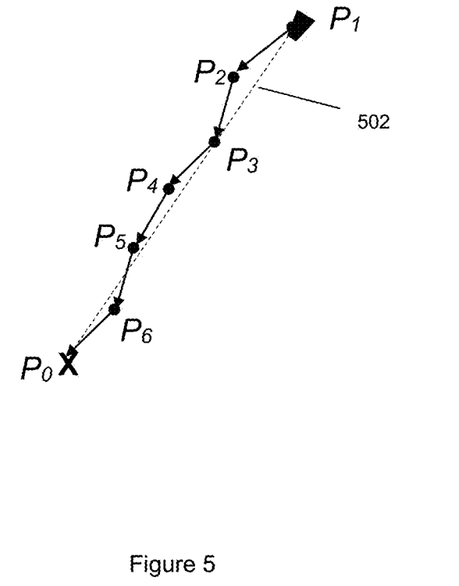
FIG. 5 shows a schematic diagram illustrating multiple positions of a distal end of surgical tool in Euclidean space on respective X-ray images when the surgical tool is being adjusted to align with a target according to an example embodiment.

FIG. 5 shows a schematic diagram of multiple positions of a distal end (i.e. tail end) of surgical tool 102 (FIG. 1) on respective X-ray images when the surgical tool 102 is being adjusted to align with a target 104 (FIG. 1) according to an example embodiment. A tip of the surgical tool 102 is placed at pivot point $P_0$ and points $P_1$ to point $P_6$ show the movement of the distal end of the surgical tool 102 on the Euclidean space when the surgical tool 102 is being adjusted. In this example, alignment occurs when the distal end of the surgical tool 102 superimposes on the pivot point $P_0$ on the X-ray image.

As can be seen from FIG. 5, each iteration reduces the image length of the surgical tool 102 and brings the longitudinal axis of the surgical tool 102 closer to the correct alignment. After each iteration, the processor 112 (FIG. 1) calculates and determines the next position of the surgical tool 102 and control an adjustment mechanism 106 (FIG. 1) to move the surgical tool 102 to the next position. The calibration of the adjustment mechanism 106 (FIG. 1) may also be determined simultaneously by the processor 112 as the iterations are carried out.

The course taken by the surgical tool 102 to align with the target may involve multiple steps. Even though the adjustment mechanism may be controlled by the processor to move the surgical tool 102 to a particular desired position, the accuracy of the position of the surgical tool 102 as moved by the adjustment mechanism 106 may be affected by the resolution of the actuator (not shown) that operates the adjustment mechanism 106. As an example, in FIG. 5, the line 502 is the desired course of the surgical tool 102 as determined by the processor 112 to align the longitudinal axis of the surgical tool 102 with the target 104 (FIG. 1). However, the actual course taken by the surgical tool 102 may show deviation. The deviation can be compensated in the movement of the surgical tool 102 in the next iteration.

Figure 6:
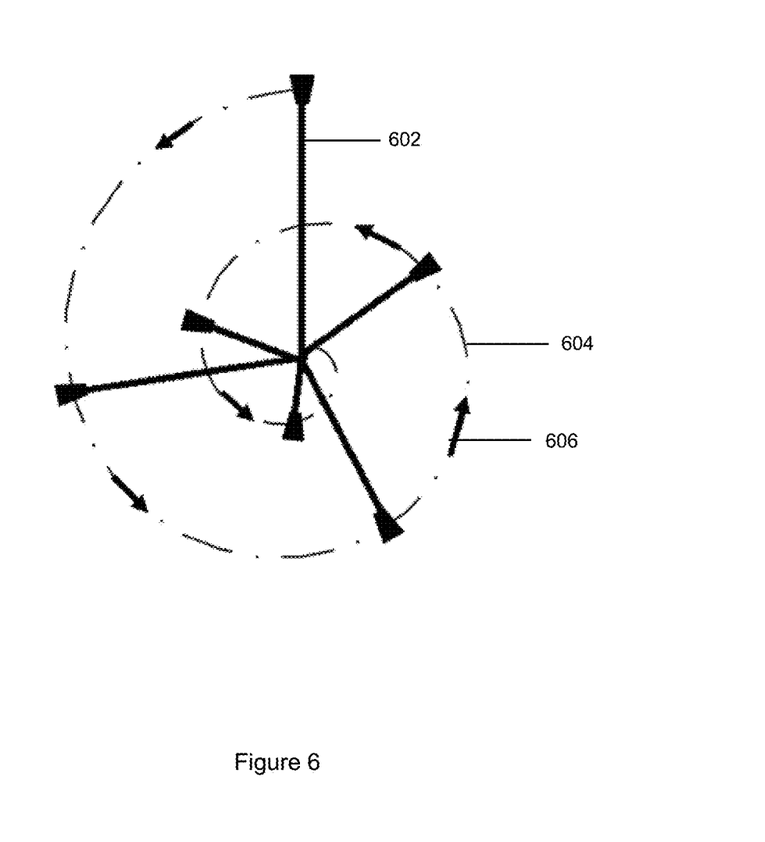
FIG. 6 shows a schematic diagram of multiple X-ray images of a surgical tool when the surgical tool is being adjusted to align with a target according to a further example embodiment.

FIG. 6 shows a schematic diagram illustrating multiple X-ray images of a surgical tool 602 when the surgical tool 602 is being adjusted to align with a target 104 (FIG. 1) according to a further example embodiment. Similar with FIG. 5, the surgical tool 602 is being adjusted in multiple iterations before it is aligned with the target 104. However, as can be seen in FIG. 6, the surgical tool 602 is being adjusted in a spiral course 604 in anti-clockwise direction to align with the target 104. The spiral movement is result of a combination of the calibration step and the surgical tool 602 adjustment step. This may reduce the total adjustment time of the surgical tool 602. The number of iterations required may be calculated by the processor 112 (not shown) based on the initial length of the Euclidean vector representing the surgical tool 602 on the X-ray image (shown at 12 o'clock position on FIG. 6). Thereafter, the iterations are automatically implemented. The movement of the surgical tool 602 in the anti-clockwise direction is shown by arrow 606.

Figure 7:
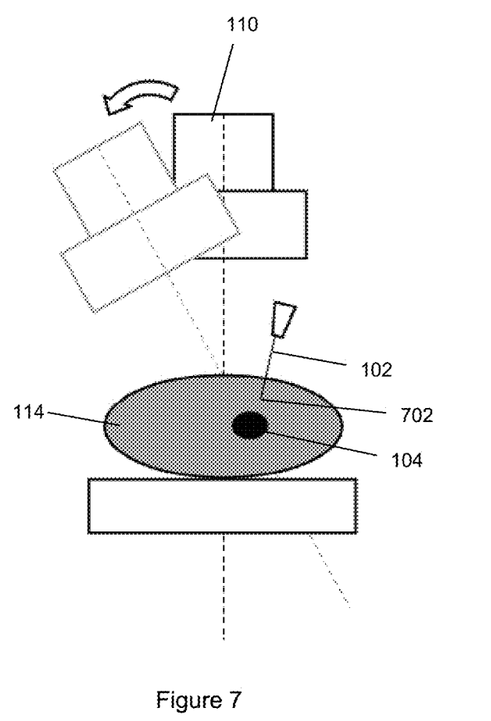
FIG. 7 shows a schematic diagram illustrating a movement of an imaging device during an operation after the surgical tool has been inserted according to an example embodiment.

FIG. 7 shows a schematic diagram illustrating a movement of an imaging device 110 during an operation after the surgical tool 102 has been inserted according to an example embodiment. As shown in FIG. 7, a tip 702 of a surgical tool 102 has been inserted into a patient's body 114. The position of the imaging device 110 may be adjusted to capture an X-ray image of the surgical tool 102 at an angle, e.g. 30° relative to the longitudinal axis surgical tool 102. From the X-ray image, a processor 112 (FIG. 1) may extract Euclidean vector data of the surgical tool 102. The distance between the tip 702 of the surgical tool 102 and a kidney stone 104 may be determined by analysing the Euclidean vector data of the surgical tool 102. The depth of the surgical tool 102 in the patient's body 114 may also be determined from the Euclidean vector data of the surgical tool 102.

Based on the analysis of the processor 112, a surgeon may manually control a plunger (not shown) of an adjustment mechanism 106 to thereby adjusting the angular orientation the surgical tool 102 into the patient's body 104 according to a step size determined by the surgeon. This process is typically repeated until the surgical tool 102 reaches the kidney stone 104.

Embodiments of the present invention provide a system for automatically aligning a surgical tool to a kidney stone. As described above with reference to the figures, the system is configured to extract the Euclidean vector data of the surgical tool during operation and adjust the angular orientation of the surgical tool to the kidney stone based on the Euclidean vector data. The system may also calibrate the movement of the adjustment mechanism by determining the relationship between the changes in the Euclidean vector data of the surgical tool for a certain movement caused by the adjustment mechanism.

Using the method and system as described in the example embodiments may reduce the operation time as compared to manually controlling the surgical tool to align with a kidney stone. As a result, the patient may subject to shorter exposure of X-ray. Since the procedure is conducted automatically by the system, the surgical crew may conduct the surgery in a separate room and not exposed to X-ray. The fact that it does not involve manually aligning the surgical tool also means that the accuracy of the alignment may be enhanced and the possibility of a successful surgery is higher.

Figure 8:
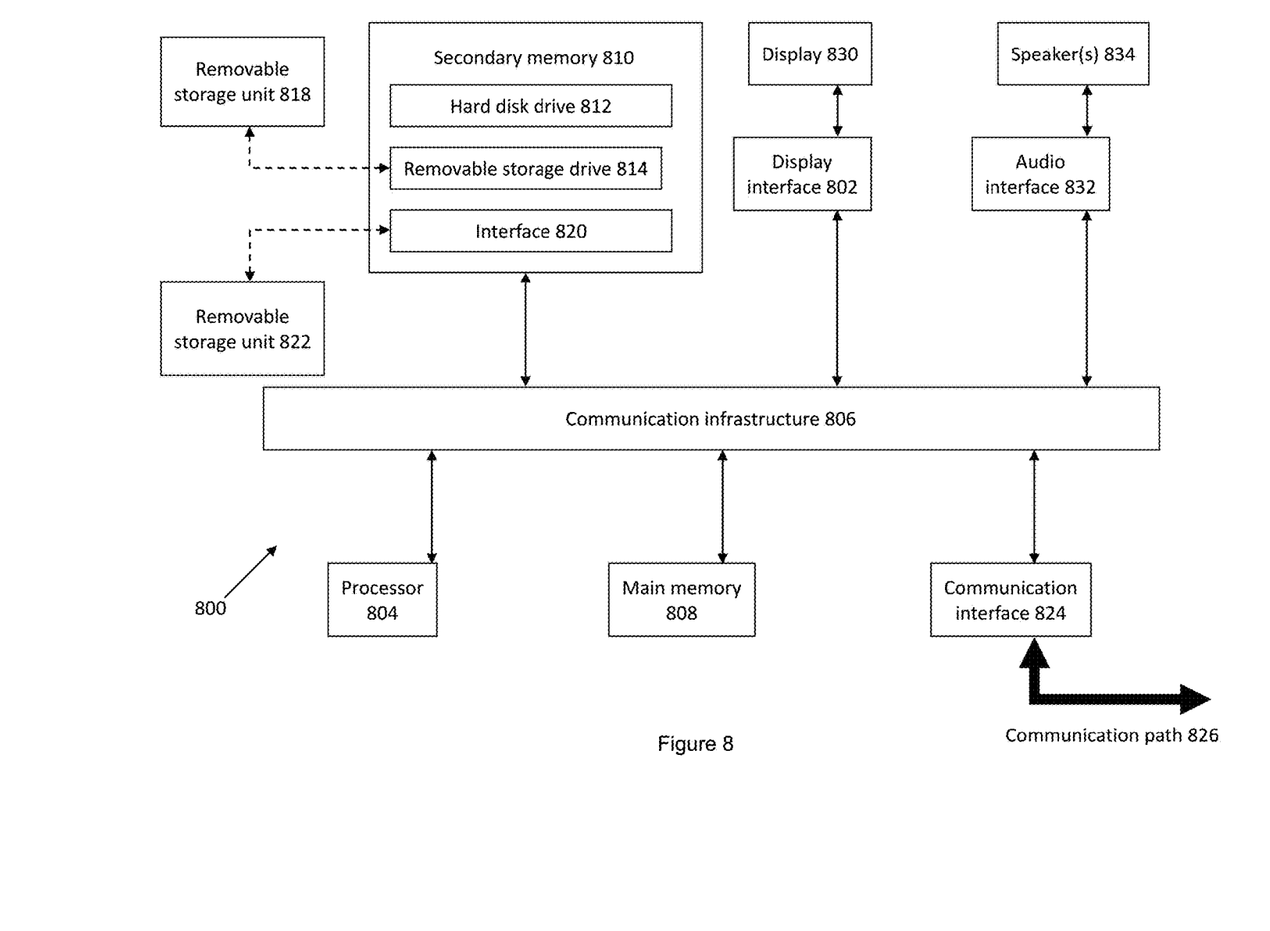
FIG. 8 shows an exemplary computing device suitable for use in the example embodiment.

FIG. 8 shows an exemplary computing device 800, hereinafter interchangeably referred to as a computer system 800, where one or more such computing devices 800 include processor (such as 112 in FIG. 1) for implementing the method and system of the example embodiments. The following description of the computing device 800 is provided by way of example only and is not intended to be limiting.

As shown in FIG. 8, the example computing device 800 includes a processor 804 for executing software routines. Although a single processor is shown for the sake of clarity, the computing device 800 may also include a multi-processor system. The processor 804 is connected to a communication infrastructure 806 for communication with other components of the computing device 800. The communication infrastructure 806 may include, for example, a communications bus, cross-bar, or network.

The computing device 800 further includes a main memory 808, such as a random access memory (RAM), and a secondary memory 810. The secondary memory 810 may include, for example, a hard disk drive 812 and/or a removable storage drive 814, which may include a floppy disk drive, a magnetic tape drive, an optical disk drive, or the like. The removable storage drive 814 reads from and/or writes to a removable storage unit 818 in a well-known manner. The removable storage unit 818 may include a floppy disk, magnetic tape, optical disk, or the like, which is read by and written to by removable storage drive 814. As will be appreciated by persons skilled in the relevant art(s), the removable storage unit 818 includes a computer readable storage medium having stored therein computer executable program code instructions and/or data.

In other embodiments, the secondary memory 810 may additionally or alternatively include other similar means for allowing computer programs or other instructions to be loaded into the computing device 800. Such means can include, for example, a removable storage unit 822 and an interface 820. Examples of a removable storage unit 822 and interface 820 include a program cartridge and cartridge interface (such as that found in video game console devices), a removable memory chip (such as an EPROM or PROM) and associated socket, and other removable storage units 822 and interfaces 820 which allow software and data to be transferred from the removable storage unit 822 to the computer system 800.

The computing device 800 also includes at least one communication interface 824. The communication interface 824 allows software and data to be transferred between computing device 800 and external devices via a communication path 826. In various embodiments of the inventions, the communication interface 824 permits data to be transferred between the computing device 800 and a data communication network, such as a public data or private data communication network. The communication interface 824 may be used to exchange data between different computing devices 800 which such computing devices 800 form part an interconnected computer network. Examples of a communication interface 824 can include a modem, a network interface (such as an Ethernet card), a communication port, an antenna with associated circuitry and the like. The communication interface 824 may be wired or may be wireless. Software and data transferred via the communication interface 824 are in the form of signals which can be electronic, electromagnetic, optical or other signals capable of being received by communication interface 824. These signals are provided to the communication interface via the communication path 826.

As shown in FIG. 8, the computing device 800 may further include a display interface 802 which performs operations for rendering images to an associated display 830 and an audio interface 832 for performing operations for playing audio content via associated speaker(s) 834.

As used herein, the term "computer program product" may refer, in part, to removable storage unit 818, removable storage unit 822, a hard disk installed in hard disk drive 812, or a carrier wave carrying software over communication path 826 (wireless link or cable) to communication interface 824. Computer readable storage media refers to any non-transitory tangible storage medium that provides recorded instructions and/or data to the computing device 800 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a SD card and the like, whether or not such devices are internal or external of the computing device 800. Examples of transitory or non-tangible computer readable transmission media that may also participate in the provision of software, application programs, instructions and/or data to the computing device 800 include radio or infra-red transmission channels as well as a network connection to another computer or networked device, and the Internet or Intranets including e-mail transmissions and information recorded on Websites and the like.

The computer programs (also called computer program code) are stored in main memory 808 and/or secondary memory 810. Computer programs can also be received via the communication interface 824. Such computer programs, when executed, enable the computing device 800 to perform one or more features of embodiments discussed herein. In various embodiments, the computer programs, when executed, enable the processor 804 to perform features of the above-described embodiments. Accordingly, such computer programs represent controllers of the computer system 800.

Software may be stored in a computer program product and loaded into the computing device 800 using the removable storage drive 814, the hard disk drive 812, or the interface 820. Alternatively, the computer program product may be downloaded to the computer system 800 over the communications path 826. The software, when executed by the processor 804, causes the computing device 800 to perform functions of embodiments described herein.

It is to be understood that the embodiment of FIG. 8 is presented merely by way of example. Therefore, in some embodiments one or more features of the computing device 800 may be omitted. Also, in some embodiments, one or more features of the computing device 800 may be combined together. Additionally, in some embodiments, one or more features of the computing device 800 may be split into one or more component parts.

It will be appreciated that the elements illustrated in FIG. 8 function to provide means for performing the various functions and operations of the servers as described in the above embodiments. In an implementation, a server may be generally described as a physical device comprising at least one processor and at least one memory including computer program code. The at least one memory and the computer program code are configured to, with the at least one processor, cause the physical device to perform the requisite operations.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A system for aligning an elongated tool to an occluded target, the system comprising:
    an adjustment mechanism configured to adjust an angular orientation of the elongated tool relative to a pivot point spaced from the target;
    an imaging device configured to capture one or more X-ray images of the elongated tool and the target; and
    a processor communicatively coupled with the adjustment mechanism and imaging device, wherein the processor is configured to:
        extract Euclidean vector data of the elongated tool based on image data of an X-ray image received from the imaging device; and
        control the adjustment mechanism to iteratively adjust the angular orientation of the elongated tool based on the Euclidean vector data to align a longitudinal axis of the elongated tool with the target and the pivot point.

2. The system as claimed in claim 1, wherein the Euclidean vector data comprises an image length of the elongated tool on an X-ray image and wherein the processor is configured to determine said image length.

3. The system as claimed in claim 2, wherein the processor is configured to:
    determine the image length of the elongated tool based on the X-ray image of the elongated tool at a first angular orientation; and
    automatically control the adjustment mechanism to adjust the elongated tool to a second angular orientation based on the image length if the image length is not approximately equal to a minimum, to iteratively align the longitudinal axis of the elongated tool with the target and the pivot point.

4. The system as claimed in claim 1, wherein the adjustment mechanism comprises a base and a platform, wherein the platform is configured to be parallel to the base.

5. The system as claimed in claim 4, wherein the adjustment mechanism further comprises a plurality of arms linking the base with the platform, the plurality of arms being configured to move the platform along a plane parallel to the base to adjust the angular orientation of the elongated tool relative to the pivot point.

6. The system as claimed in claim 4, wherein the platform comprises a ball joint compliance for supporting the elongated tool, the ball joint compliance comprising a hole configured to allow sliding movement of the elongated tool therethrough.

7. The system as claimed in claim 6, wherein the base of the adjustment mechanism is made of a radiopaque material and wherein remaining components of the adjustment mechanism are made of one or more radiolucent materials.

8. The system as claimed in claim 1, wherein the imaging device is a C-arm fluoroscope configured to capture real-time X-ray images.

9. The system as claimed in claim 1, wherein the adjustment mechanism further comprises at least one actuator communicatively coupled with the processor, the actuator being configured to operate the arms.

10. A method of aligning an elongated tool to an occluded target, the method comprising the steps of:
    capturing one or more X-ray images of the elongated tool and the target;
    extracting Euclidean vector data of the elongated tool based on image data of an X-ray image; and
    iteratively adjusting an angular orientation of the elongated tool relative to a pivot point based on the Euclidean vector data to align a longitudinal axis of the elongated tool with the target and the pivot point.

11. The method as claimed in claim 10, wherein the Euclidean vector data comprises an image length of the elongated tool on an X-ray image.

12. The method as claimed in claim 11, wherein adjusting an angular orientation comprises the steps of:
    determining the image length of the elongated tool based on the X-ray image at a first angular orientation; and
    automatically controlling the adjustment mechanism to adjust the elongated tool to a second angular orientation based on the image length if the image length is not approximately equal to a minimum, to iteratively align the longitudinal axis of the elongated tool with the target and the pivot point.

13. The method as claimed in claim 10, further comprising a step of calibrating a geometrical relationship between an imaging device capturing the one or more X-ray images and an adjustment mechanism adjusting the angular orientation of the elongated tool.

14. The method as claimed in claim 13, wherein the step of calibrating comprises determining the number of iterations to reach the minimum from an initial image length.

15. The method as claimed in claim 13, wherein the adjustment mechanism comprises a base and a platform parallel to the base, and the step of calibrating comprises fixing a height of the platform from the base.

16. A method of striking an occluded target using an elongated tool, the method comprising the step of:
    iteratively advancing the elongated tool toward the target, wherein iteratively advancing the tool comprises aligning the tool to the target at each iteration using the method as claimed in claim 10.

17. The method as claimed in claim 16, further comprising a step of determining a distance between a tip of the tool and target after a predetermined number of iterations.

* * * * *

UNITED STATES PATENT AND TRADEMARK OFFICE
CERTIFICATE OF CORRECTION

PATENT NO. : 10,226,300 B2
APPLICATION NO. : 15/211724
DATED : March 12, 2019
INVENTOR(S) : Ka Wei Ng et al.

Page 1 of 1

It is certified that error appears in the above-identified patent and that said Letters Patent is hereby corrected as shown below:

On the Title Page

Item (30), please add:
Foreign Application Priority Data
Jul 15, 2015 (SG) 10201505560Y Signed and Sealed this
Twenty-fourth Day of September, 2019

Andrei Iancu
*Director of the United States Patent and Trademark Office*